(12) United States Patent
Greydanus et al.

(10) Patent No.: US 7,198,620 B2
(45) Date of Patent: Apr. 3, 2007

(54) ONE STAGE SALINE LOCK AND INTRAVENOUS CATHETER SET AND METHOD OF USE

(75) Inventors: Dominique J. Greydanus, Fort Sam Houston, TX (US); John Kennedy, Boeblingen (DE); John B. Holcomb, San Antonio, TX (US); Robert Miller, Simpsonville, SC (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/986,810

(22) Filed: Nov. 15, 2004

(65) Prior Publication Data

US 2005/0197635 A1 Sep. 8, 2005

Related U.S. Application Data

(60) Provisional application No. 60/519,330, filed on Nov. 13, 2003.

(51) Int. Cl.
*A61M 25/00* (2006.01)
(52) U.S. Cl. .................................... 604/284
(58) Field of Classification Search ............... 604/82, 604/158, 164, 165, 166.01, 167, 284, 264, 604/523
See application file for complete search history.

(56) References Cited

U.S. PATENT DOCUMENTS 4,099,528 A * 7/1978 Sorenson et al. ............ 604/44
4,333,455 A * 6/1982 Bodicky ..................... 604/158
4,585,435 A * 4/1986 Vaillancourt ................ 604/518
4,798,605 A 1/1989 Steiner et al.
4,998,927 A 3/1991 Vaillancourt
5,071,405 A * 12/1991 Piontek et al. ......... 604/103.03
5,098,410 A * 3/1992 Kerby et al. ................ 604/256
5,236,417 A * 8/1993 Wallis ......................... 604/82
5,254,097 A * 10/1993 Schock et al. ......... 604/167.04
5,290,244 A * 3/1994 Moonka ................. 604/164.13
5,358,490 A * 10/1994 Henry et al. ........... 604/167.03
5,509,908 A * 4/1996 Hillstead et al. ............ 604/264
5,591,137 A 1/1997 Stevens
5,749,857 A 5/1998 Cuppy
5,810,793 A * 9/1998 Boettger ..................... 604/284
5,911,710 A 6/1999 Barry et al.
6,331,176 B1 12/2001 Becker et al.
6,533,759 B1 3/2003 Watson et al.
6,569,125 B2 5/2003 Jepson et al.
6,572,593 B1 6/2003 Daum
6,921,391 B1 * 7/2005 Barker et al. ............... 604/284

* cited by examiner

*Primary Examiner*—Manuel Mendez
(74) *Attorney, Agent, or Firm*—Elizabeth Arwine

(57) ABSTRACT

The invention is a saline lock and intravenous catheter combination that is simple to use. The device preferably includes a hub and a catheter with the hub having a first port and a second port. A further embodiment provides a needle in communication with the device. The invention also includes a method for using the device in combination with a needle.

15 Claims, 1 Drawing Sheet

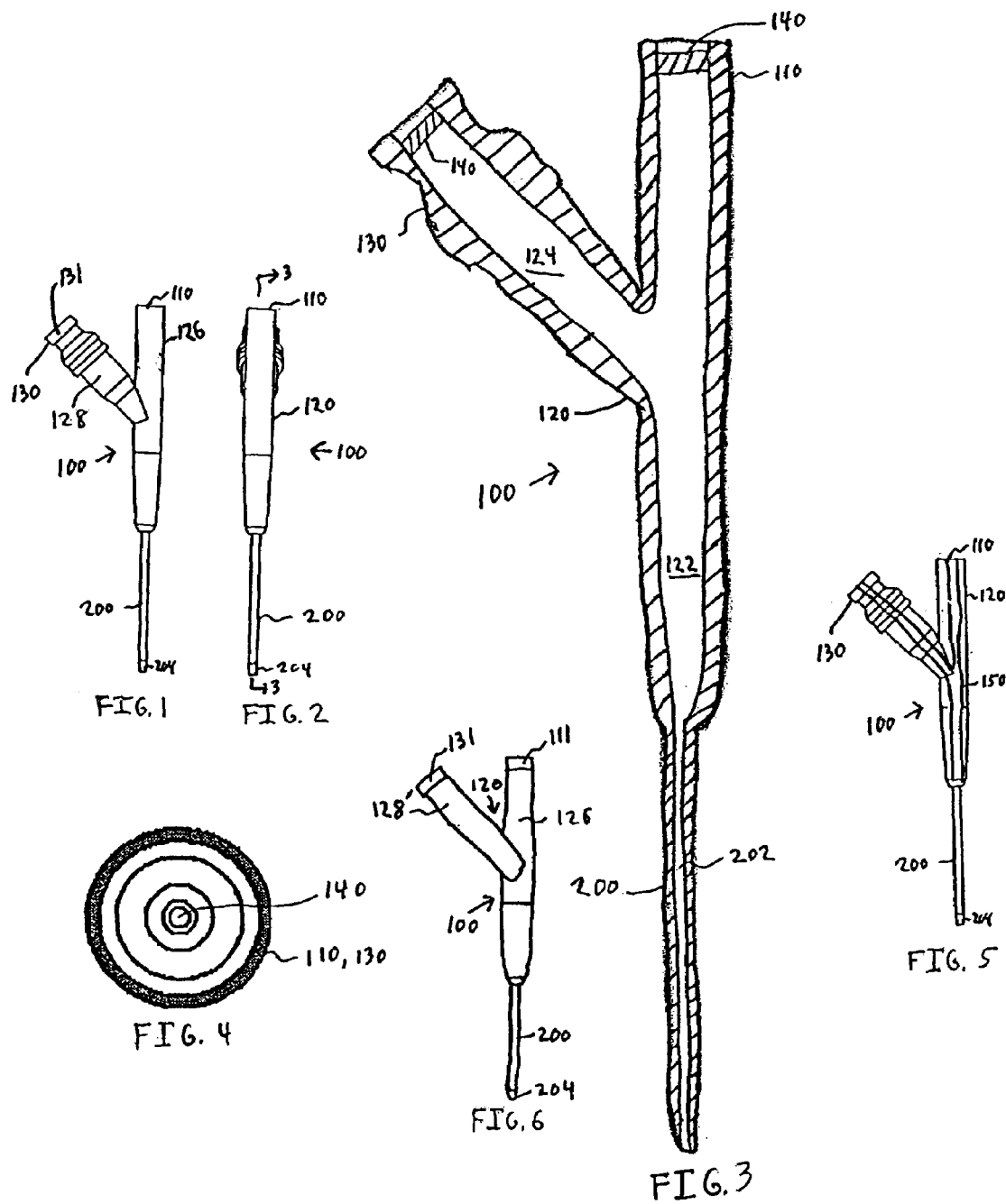

ONE STAGE SALINE LOCK AND INTRAVENOUS CATHETER SET AND METHOD OF USE

This application claims the benefit of U.S. provisional application Ser. No. 60/519,330, filed on Nov. 13, 2003, which is incorporated herein by reference.

I. FIELD OF THE INVENTION

This invention relates to a device and method for allowing medical personnel to simultaneously provide medication and intravenous fluid to a patient through the same catheter.

II. BACKGROUND OF THE INVENTION

Establishing an intravenous (IV) fluid for a hydrated patient is not a difficult task in a hospital setting with plenty of light, the required tools and equipment readily available in an organized arrangement. However, as the setting and environment change from a safe, sterile, low stress environment of a hospital to a combat zone where bullets are whizzing overhead and shells are exploding around a medic, the difficultly increases with the number of changes from the hospital setting. When the level of light is decreased to what is available from the stars, it becomes a bit tricky to locate the required equipment and see where the insertion site on a patient might be. The last thing the medic wants to do is turn on a white light and announce to the enemy where he/she is for target practice. When the patient is wounded and bleeding, locating a usable blood vessel (let alone any blood vessel) becomes even trickier, because the loss of blood leads to a reduced volume of blood circulating that, in turn, constricts the blood vessels and the slippery conditions that might exist around the potential IV sites. If the combat soldier or other individual has been in the field and has not maintained hydration levels, the soldier is likely to by dehydrated, which will further constrict the blood vessels of the patient. If the patient is a combat soldier or other individual with a full set of gear that needs to be removed, then valuable time will be consumed removing the necessary gear prior to beginning the IV, which increases the pressure to efficiently and quickly begin the IV. The ability to establish an IV becomes more difficult for each of the above conditions existing in the environment in which the IV is being established.

The last thing that the medic wants to do is remove (or disconnect) the IV for moving (or evacuating) the patient to a medical facility, because of the difficulty to establish the initial IV. Instead of disconnecting the IV, the alternative is to establish a saline lock, which requires at a minimum a saline lock, an 18 g–1.5" needle, a 10 cc syringe, saline, and a 4"—4" Tegaderm patch to cover it. Assuming that the supplies are available, under the best of circumstances it will take one to three minutes to install and establish the saline lock for transport, which means if any of the conditions describe above exist the time to do this will increase tremendously. Even assuming the saline lock is established, it is inevitable that it will begin to leak where the IV hub connects with the IV catheter, for example, due to vibrations from the evacuation vehicle (such as an HUMVEE ambulance, a civilian ambulance, a helicopter or other vehicle) or the patient being transported over rough terrain.

Furthermore, establishing a saline lock is complicated and not conducive to being performed in the field under environmental pressures such as during a gun battle. A typical IV catheter includes a needle that extends out beyond the IV catheter tip to allow the needle to puncture a patient's skin and blood vessel wall. The process begins with inserting the needle through the skin and into a blood vessel such as a vein of the patient, and then threading the IV catheter down the needle further into the blood vessel to secure the IV catheter in the blood vessel. The saline lock then is attached to the back of the IV catheter thus requiring multiple pieces of medical equipment of small size to be interconnect. The alternative is to attach the saline lock to the IV catheter with the insertion needle passing through both pieces, which requires both pieces to have a diaphragm to prevent leakage. In the field in the middle of a battle and/or gunfight, there is not the time or calmness to install a catheter, connect the catheter to an IV (either directly or via a hub), and attach a saline lock in line between the catheter and the IV tube. The size and number of components increase the likelihood that dirt and other environmental containments will become lodge between the pieces and provide a ready contamination source.

Additionally if the IV remains connected to the patient, when the patient is moved particularly in a military setting, no matter how many precautions are taken by the medic when preparing the patient for transport and/or extraction, a branch, vehicle door or some other object ends up catching the attached IV tubing and ripping the IV out of the patient. If the IV tubing is ripped out, then the patient is able to bleed out through the catheter that will likely remain inserted in the patient and providing a pathway for blood to flow out the patient unless plugged/clogged up or removed from the patient. If the patient is not conscious or the medics are distracted, then the bleeding can add to the loss of blood and increase the likelihood of death.

Furthermore, currently used IV plugs (or saline locks) without exception start to leak after any kind of movement, which compromises the IV site on an injured patient both in terms of leakage from the patient and/or IV and containments making there way into the patient via the leak area.

Notwithstanding the usefulness of the above-described methods, a need still exists for a simpler way to install a saline lock and IV catheter including a more compact, simpler device.

III. SUMMARY OF THE INVENTION

This invention provides a device that is compact and easy to use having a hub component with two branches allowing, for example, administration of an IV and/or medication to the patient via a catheter in fluid communication with the two branches. More preferably, the catheter is unitarily formed as one piece with the hub allowing for a simplified use of the invention. The invention also includes a method for using the device.

According to at least one embodiment of the invention, the invention includes an apparatus comprising a hub having a body having a central passageway passing therethrough and a branch passageway passing therethrough in communication with the central passageway, the body having a means for connecting to an IV, the means in communication with the central passageway, a medication port in communication with the branch passageway, and a catheter extending from an end of the body opposite the first port.

According to at least one embodiment of the invention, the invention includes an apparatus comprising a hub having a body having a central passageway passing therethrough and a branch passageway passing therethrough in communication with the central passageway, the body having a first port at one end, the first port in communication with the central passageway, a second port in communication with the branch passageway, and a catheter extending from an end of the body opposite the first port. According to at least one embodiment, the invention includes a system having the apparatus and a needle in communication with the apparatus. According to at least one embodiment, the invention includes a method for using the system comprising inserting the needle into a blood vessel of a patient a sufficient depth to fix the catheter in the blood vessel, removing the needle from the blood vessel, the catheter, and the body, and attaching an IV to the first port to begin the administration of an IV.

An objective of at least one embodiment of the invention is to simplify the installation process and the number of components for establishing an IV.

Another objective of at least one embodiment of the invention is to allow the military medic to save time and lives by having the ability to leave a patient catheter in place while moving the patient in austere environments.

Another objective of at least one embodiment of the invention is to expedite the ability of the medical provider to administer life saving fluids and medication to patients.

Another objective of at least one embodiment of the invention is the medical provider will be able to administer various medications via one port and able to run. IV fluids thru a second port without the need for a T-device.

The above objectives lead to a variety of advantages.

An advantage of at least one embodiment of the invention is a decrease in the cost of resupply and the number of items in the medic's bag.

Another advantage of at least one embodiment of the invention is that medical personnel have an instant saline lock without other attachments being needed to attach to the patient.

Another advantage of at least one embodiment of the invention is that the medication port is easily and quickly flushed with saline.

Another advantage of at least one embodiment of the invention is that the medical provider can discontinue the IV infusion without having to remove the catheter during patient movement.

Another advantage of at least one embodiment of the invention is easy identification of the ports for attaching, for example, an IV and/or medication delivery device such as syringe or tube.

Given the following enabling description of the drawings, the apparatus should become evident to a person of ordinary skill in the art.

IV. BRIEF DESCRIPTION OF THE DRAWINGS

The present invention is described with reference to the accompanying drawings. In the drawings, like reference numbers indicate identical or functionally similar elements. The use of cross-hatching and shading within the drawings is not intended as limiting the type of materials that may be used to manufacture the invention. The figures are not drawn to scale.

FIG. 1 illustrates a side view of one exemplary embodiment according to the invention.

FIG. 2 depicts another side view of the embodiment illustrated in FIG. 1.

FIG. 3 illustrates an enlarged cross-section of FIG. 2 as indicated in FIG. 2 with reference line 3—3.

FIG. 4 depicts a top view of a portion of at least one exemplary embodiment according to the invention.

FIG. 5 illustrates an exemplary embodiment according to the invention.

FIG. 6 depicts an exemplary embodiment according to the invention.

V. DETAILED DESCRIPTION OF THE DRAWINGS

The invention preferably includes a unitary device with an IV port, a medication port, a hub, and a catheter. The IV port and the medication port preferably are in fluid communication with the hub, which in turn is in fluid communication with the catheter. The invention in at least one embodiment includes a pre-inserted needle through the IV port, the hub, and the catheter to allow for quicker insertion into a patient during initial care. Quicker insertion is achieved because the medical professional does not need to pull from his/her medical kit a catheter and a needle, and then pass the needle through the catheter prior to insertion. Additional time savings are obtained after the catheter is inserted from the unitary construction because the IV port (or saline lock) is attached already and does not need to be attached, and in at least one embodiment the needle can be removed because the IV port includes a diaphragm (or other sealant material). Once the needle is removed, an IV can be started for the patient by attaching the IV bag to the IV port.

FIGS. 1–3 illustrate an exemplary embodiment according to the invention that includes a hub 100 and a catheter 200. The hub 100 includes an IV port (or means for connecting to an IV or first port) 110 at one end of a body 120 with the catheter 200 extending from the other end of the body 120. The catheter 200 forms a unitary piece with the hub 100 such that they form one piece and the medical professional does not need to connect them together. As illustrated in FIGS. 1–3, the passageway running from the IV port 110 to the catheter 200 is straight for insertion of a needle into the catheter 200. The centers of the passageway in the catheter 200, the body 120, and the IV port 110 are axially aligned as illustrated. The body 120 includes a second port (or medication port) 130 extending from a side as shown, for example, in FIG. 1. In the exemplary embodiment illustrated in FIG. 3, both the IV port 110 and the second port 130 include a diaphragm 140 or other rubber seal (such as a rubber septum) that is self-sealing. FIG. 4 illustrates a top view of the ports 110, 130 with the diaphragm 140 present inside the passageway 122, 124. Both the IV port 110 and the second port 130 in at least one embodiment include connectors such as Luer-lock connectors to facilitate attachment to syringes and/or catheters (or other tubing). FIG. 1 illustrates the second port 130 having a connector 131. FIG. 6 illustrates the IV port 110 having a connector 111.

The body 120 includes a passageway (or central passageway) 122 passing through it that runs from the IV port 110 to the catheter 200 with the catheter 200 having a passageway 202 in fluid communication with the passageway 122 of the body 120 such that liquid may pass from the IV port 110 through the body 120 into the catheter 200 and into the patient. The body 120 also includes a passageway branch 124 (in the branch (or branch portion) 128) that runs from the central passageway 122 (in the central body (or central portion) 126) to the second port 130 thus providing a channel for fluid to travel from the second port 130 through the body 120 and the catheter 200.

The invention in an exemplary embodiment is about 3.25" in length from the tip of the catheter to the IV port; however, the length can vary depending upon the catheter size and/or anticipated patient size, for example. The branch 128 extends at an angle from the central body 126 with its opening facing away from the catheter 200 in the illustrated exemplary embodiments. An exemplary angle is a 45-degree angle as illustrated, for example, in FIGS. 1 and 3.

In at least one embodiment of the invention, the body 120 and the IV port 110 are color coded to coincide with IV catheters used currently. This allows for a quicker determination that the port 110 is for an IV as opposed to the second multipurpose port 130. The second port 130 during use preferably is a medication port that would be, for example, color-coded white as not to be confused with the IV port 110.

FIG. 5 illustrates an exemplary embodiment that has a window 150 running the length of the central body 126 and along the branch 128 leading to the second port 130. The window preferably is a clear material to allow the medical professional to easily determine whether fluid is flowing through the hub from the IV and/or the medication source. Further alternatives would be to have the window at selected spot or spots on the body 120 or along a portion of the length of the central body 126 and/or branch 128. Alternatively, the entire body 120 may be constructed of a clear material, and if combined with the color coded embodiment described above the body 120 may be tinted the appropriate color.

FIG. 6 illustrates an exemplary embodiment of the invention where branch 128' is straight from the central body 126 to the second port 130. This exemplary embodiment is offered to illustrate that the outside shape of the branch 128' may be a variety of shapes without impacting the underlying inventive concept.

The method for inserting the invention into the patient includes passing a needle such as a beveled venous puncture needle through the IV port 110, the body 120 and the catheter 200 such that it extends beyond the tip 204 of the catheter 200. Alternatively, the needle may be packaged already inserted into the device to simplify the use of the device in the field (not illustrated). Inserting the needle into a blood vessel of the patient to secure the catheter 200 in the blood vessel. Once the catheter 200 is secured, removing the needle. The IV is then attached to the IV port 110 and medication or other fluid may be administered through the second port 130 as desired/needed. The second port 130 also allows for the port to be flushed with saline after, for example, medication is provided through the port.

Although the present invention has been described in terms of particular exemplary embodiments, it is not limited to those embodiments. Alternative embodiments, examples, and modifications which would still be encompassed by the invention may be made by those skilled in the art, particularly in light of the foregoing teachings. The exemplary and alternative embodiments described above may be combined in a variety of ways with each other. Furthermore, the dimensions, shapes, sizes, and number of the various pieces illustrated in the Figures may be adjusted from that shown.

Furthermore, those skilled in the art will appreciate that various adaptations and modifications of the above-described exemplary embodiments can be configured without departing from the scope and spirit of the invention. Therefore, it is to be understood that, within the scope of the appended claims, the invention may be practiced other than as specifically described herein.

We claim:

1. A one stage saline lock and intravenous catheter system comprising:
   a hub having
      a body having a central passageway passing therethrough and a branch passageway passing therethrough in fluid communication with the central passageway, said body having
         a first port at one end of said body, said first port in fluid communication with the central passageway, said first port includes a diaphragm, and
         a second port in fluid communication with the branch passageway, said second port is spaced along said body from said first port, said second port includes a diaphragm;
   a catheter extending from an end of said body opposite said first port, said catheter including a passageway passing therethrough, the passageway in fluid communication with the central passageway of said body, the passageway running from said catheter to said body to said first port is axially aligned;
   said body and said catheter are integrally formed together as an unitary piece; and
   a needle passing through said first port and said hub and through said catheter.

2. The system according to claim 1, wherein said first port is configured to attach to an IV.

3. The system according to claim 2, wherein said second port is configured to attach to a syringe or a tube.

4. The system according to claim 3, wherein said body includes a central portion connected to said first port and a branch portion connected to said second port.

5. The system according to claim 3, wherein at least one of said first port and said second port includes a Luer-lock connector or other connection means.

6. The system according to claim 1, wherein the diaphragm is spaced from the end of said first port and/or said second port.

7. The system according to claim 6, wherein the body further includes a window running the length of at least one of the central passageway and the branch passageway.

8. The system according to claim 1, wherein each diaphragm is spaced from a respective end of said first port and said second port.

9. The system according to claim 1, wherein at least one of said first port and said second port are color coded for identification purposes.

10. The system according to claim 1, wherein said needle is a beveled venous puncture needle.

11. The system according to claim 1, wherein the body further includes a window running the length of at least one of the central passageway and the branch passageway.

12. The system according to claim 1, wherein the length of said body with said catheter is no more than 3.5 inches long.

13. An apparatus comprising:
   a hub having
      a body having
         a central body having a central passageway passing therethrough, the central passageway is straight,
         a branch body having a branch passageway passing therethrough in communication with the central passageway,
         a first port at one end of said central body, said first port in communication with the central passageway,
         a second port in communication with the branch passageway, said second port is spaced along said central body from said first port, and
         a window running the length of at least one of the central body and the branch; and
   a catheter extending from an end of said body opposite said first port, said catheter including a passageway passing therethrough, the passageway in communication with the central passageway of said body to form a straight passageway running from said first port to a free end of said catheter, and said body is integrally formed with said catheter, at least one of said first port and said second port includes a Luer-lock connector or other connection means, at least one of said first port and said second port includes a diaphragm spaced from the end of said port, and said hub and said catheter together have a length no more than 3.5 inches.

14. The apparatus according to claim 13, wherein the branch passageway is in fluid communication with the central passageway, and the central passageway is in fluid communication with the passageway of said catheter.

15. An saline lock and intravenous catheter set consisting of a catheter, a hub integrally formed with said catheter, said hub having a body in communication at one end with said catheter, said body having a first port at one end of said body opposite said catheter, and a second port located along said body between said first port and said catheter, said body having a passageway that fluidly connects said catheter with said first port and said second port, the passageway running from said first port to said catheter is straight, said first port having a connector and a diaphragm within the passageway spaced from said connector, and said second port having a connector and a diaphragm within the passageway spaced from said connector.

* * * * *